(12) United States Patent
Anand et al.

(10) Patent No.: US 11,904,128 B2
(45) Date of Patent: Feb. 20, 2024

(54) FLUID DELIVERY SYSTEM

(71) Applicant: ALCYONE THERAPEUTICS, INC., Lowell, MA (US)

(72) Inventors: PJ Anand, Lowell, MA (US); Deep Arjun Singh, Cambridge, MA (US); Andrew East, Lowell, MA (US); Thomas T. Washburn, Lancaster, MA (US); Megan Holmes, Cambridge, MA (US)

(73) Assignee: ALCYONE THERAPEUTICS, INC., Lowell, MA (US)

( * ) Notice: Subject to any disclaimer, the term of this patent is extended or adjusted under 35 U.S.C. 154(b) by 593 days.

(21) Appl. No.: 17/004,470

(22) Filed: Aug. 27, 2020

(65) Prior Publication Data
US 2021/0060326 A1 Mar. 4, 2021

Related U.S. Application Data

(60) Provisional application No. 62/893,034, filed on Aug. 28, 2019.

(51) Int. Cl.
| | |
|---|---|
| A61M 39/02 | (2006.01) |
| A61M 39/10 | (2006.01) |
| A61M 39/00 | (2006.01) |
| A61M 39/06 | (2006.01) |

(52) U.S. Cl.
CPC . *A61M 39/0208* (2013.01); *A61M 2039/0072* (2013.01); *A61M 2039/0235* (2013.01); *A61M 2039/062* (2013.01); *A61M 2039/1033* (2013.01)

(58) Field of Classification Search
CPC ...... A61M 39/0208; A61M 2039/0072; A61M 2039/062; A61M 2039/1033
See application file for complete search history.

(56) References Cited

U.S. PATENT DOCUMENTS

| | | | |
|---|---|---|---|
| 4,569,675 | A | 2/1986 | Prosl et al. |
| 4,704,103 | A | 11/1987 | Stober et al. |
| 4,929,243 | A | 5/1990 | Koch et al. |
| 6,458,103 | B1 | 10/2002 | Albert et al. |
| 8,366,675 | B2 | 2/2013 | Saitoh et al. |
| 10,231,727 | B2 | 3/2019 | Sutherland et al. |
| 2005/0095891 | A1 | 5/2005 | Schorn |
| 2011/0208129 | A1 | 8/2011 | Bonnette et al. |
| 2016/0287783 | A1 | 10/2016 | Zhao et al. |

FOREIGN PATENT DOCUMENTS

| | | |
|---|---|---|
| CN | 103705279 A | 4/2014 |
| CN | 110022916 A | 7/2019 |
| EP | 0332943 A1 | 9/1989 |
| EP | 0496991 A1 | 8/1992 |
| FR | 2628639 A1 | 9/1989 |

OTHER PUBLICATIONS

International Application No. PCT/US20/47726, International Search Report and Written Opinion, dated Nov. 23, 2020.
European U.S. Appl. No. 20/857,614, Supplementary European Search Report, completed Jul. 28, 2023.

*Primary Examiner* — Bradley J Osinski
(74) *Attorney, Agent, or Firm* — MARSHALL, GERSTEIN & BORUN LLP

(57) ABSTRACT

The fluid delivery devices, systems and methods described herein include a subcutaneous port, a catheter, and a connection assembly configured to fluidly couple the port and catheter.

21 Claims, 5 Drawing Sheets

FLUID DELIVERY SYSTEM

CROSS-REFERENCE TO RELATED APPLICATION

This application claims the priority benefit of U.S. Provisional Application No. 62/893,034, filed Aug. 28, 2019, which is hereby incorporated by reference herein in its entirety.

FIELD OF THE DISCLOSURE

The present disclosure generally relates to fluid delivery systems and, more particularly, to port and catheter fluid delivery systems.

BACKGROUND

Intrathecal administration is a valuable tool for introducing therapeutic agents into the cerebral spinal fluid (CSF), which allows distribution throughout the central nervous system. Indeed, therapeutics administered to CSF are distributed to the brain and spinal cord, thereby avoiding potential delivery issues through the blood-brain barrier. Most drugs delivered to the CSF require multiple administrations, requiring at least periodic access to the intrathecal space over the course of a treatment regimen. Some individuals are unable to receive medication via lumbar puncture due to anatomical barriers, such as spinal deformities, and/or surgical interventions, such as implantation of stabilizing rods and spondylosis. Bone fusions, sharp angles, and instrumentation in these individuals complicate or prevent direct lumbar puncture entry into the intrathecal space because there is no space between the bones to allow safe puncture of the dura. In these patients, extraordinary means are often required to achieve intrathecal access; for example, an oscillating drill may be required to bore through the bone mass or a laminectomy procedure may be required, which heightens the risk associated with intrathecal administration. There remains a need in the art for a delivery system that allows repeated administration of substances to the intrathecal space.

SUMMARY

In accordance with a first aspect, a fluid delivery system is disclosed that includes a body defining a cavity therein, where the cavity has a cylindrical configuration with a delivery opening at a proximal end and an open distal end. The cavity defines a seat surface that extends radially inwardly into the cavity adjacent to the delivery opening and a threaded portion adjacent to the open distal end. The fluid delivery system further comprises a catheter connection assembly that is disposed within the cavity and is configured to couple a catheter to the body. The catheter connection assembly includes a washer that is configured to abut the seat surface, a gasket, an engagement tip disposed on an opposite side of the gasket from the washer, and a connector having an external thread that is configured to engage the threaded portion of the cavity. The washer, gasket, engagement tip, and connector each define a central passage extending therethrough for reception of a catheter, and the catheter connection assembly is configured such that when the connector is threaded into the cavity, the connector causes the engagement tip and washer compress the gasket therebetween to thereby radially compress the gasket around the catheter to retain the catheter within the cavity.

According to some forms, the cavity comprises an inner portion extending from the seat surface to the delivery opening and the catheter connection assembly further comprises a stem member having a base portion and a stem portion extending outwardly from the base portion. The stem member is configured to be disposed within the inner portion of the cavity such that the stem portion extends longitudinally within the cavity away from the delivery opening into a catheter that is inserted through the washer, gasket, engagement tip, and connector. In further forms, the stem portion can have a length to extend through the washer and gasket and into the central passage of the engagement tip, such that the stem portion braces a catheter along a portion thereof compressed by the gasket when then connector is threaded into the cavity and/or the inner portion of the cavity and the base portion of the stem member can have complementary contoured surfaces, such that the base seats within the inner portion of the cavity and is restricted from longitudinal movement within the cavity toward the delivery opening.

According to some forms, the fluid delivery system can include one or more of the following aspects: the gasket can be a plurality of o-rings; the seat surface of the cavity can extend rearwardly along a longitudinal axis thereof and an inner surface of the washer can have a complementary chamfered configuration such that the washer nests within the seat surface; or the connector can include a throat portion having a reduced diameter as compared to the threaded portion; and the body further comprises a bore opening radially into the cavity; and further comprising a retention member configured to be inserted into the bore to extend along the throat portion rearwardly of the threaded portion to thereby retain the connector within the cavity According to some forms, compression surfaces of the engagement tip and the washer engage the gasket on opposite sides thereof and at least one of the compression surfaces of the engagement tip and the washer can have a contoured configuration extending away from the gasket to thereby provide deformation space for the gasket as the gasket is compressed. In further forms, the compression surfaces of both the engagement tip and the washer can have contoured configurations extending away from the gasket to thereby provide deformation spaces for the gasket on both sides thereof, the compression surface of at least one of the engagement tip can have a bulleted configuration, and/or the compression surface of at least one of the engagement tip can have a chamfered configuration.

According to some forms, the engagement tip and the connector can be a single-piece component. According to other forms, the engagement tip and connector can be separate components. So configured, in further forms, the engagement tip and connector can have a stepped connection therebetween, one of the engagement tip or the connector comprising a counterbore and the other of the engagement tip or the connector comprising a collar configured to be received within the counterbore.

According to some forms, the connector can include a tool engagement end having a diameter larger than the cavity such that the tool engagement end defines a stop surface configured to engage the body when the connector is fully threaded into the cavity. In a further form, the central passage extending through the tool engagement end of the connector can have a fluted configuration; and/or an exterior radial surface of the tool engagement end can include ribs and the system can include a wrench having a mouth configured to extend around the tool engagement end, an interior surface of the mouth comprising indentations configured to engage the ribs of the tool engagement end such that the wrench is configured to tighten the connector into the cavity. If desired, the ribs and indentations can be configured to slip out of engagement with one another upon the application of a rotational force to the wrench greater than a threshold force.

According to some forms, the body can be a port implantable to a subcutaneous location, where the port defines a chamber having an open top and the delivery opening and a septum extending over the open top of the chamber. In a further form, the system can include a catheter that extends through the washer, gasket, engagement tip, and connector, where the gasket is compressed around a proximal end of the catheter to retain the catheter within the cavity and fluidly couple the catheter to the chamber of the port.

In accordance with a second aspect, a method of assembly of any of the above fluid delivery systems is described herein.

DETAILED DESCRIPTION

The fluid delivery devices, systems and methods described herein include a sterile, implantable intrathecal catheter and subcutaneous port. The fluid delivery devices are designed to facilitate intrathecal access in patients with normal spines, as well as patients with spinal deformities and/or instrumentation for whom intrathecal access, and the associated fluid administration and sampling, via lumbar puncture (LP) is complicated or not possible. By utilizing the devices, systems, and methods provided, the need for repeat anesthesia and surgery each time intrathecal access is needed in these patients can be avoided.

The fluid delivery systems can be used to administer fluids (optionally including one or more therapeutic agents) to patients by means of manual bolus injection, standard syringe pump or Pulsar auto-injector pump. Therapeutics approved for bolus intrathecal administration would be infused into the patient through the subcutaneous port by palpating the port to identify the septum, and accessing the septum with a needle, such as a standard non-coring Huber needle.

Figure 1:
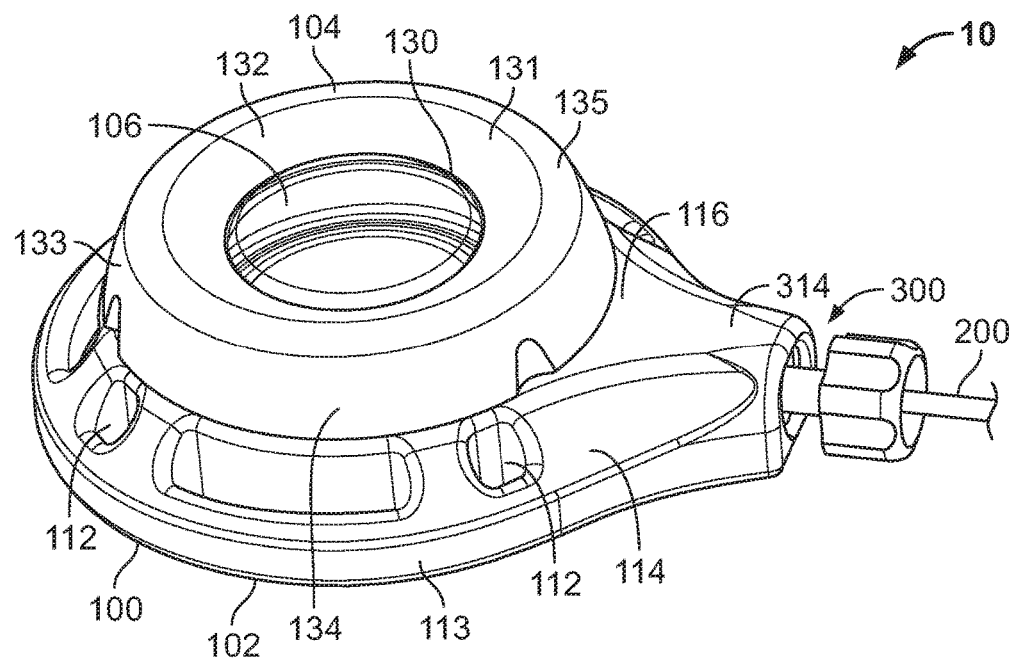
FIG. 1 is a perspective view of an example fluid delivery system including a port, a catheter, and a connection assembly in accordance with various embodiments.

A fluid delivery system 10 is shown in FIGS. 1-11 that includes a port 100, a catheter 200, and a connection assembly 300 configured to fluidly couple the port 100 and catheter 200. An example configuration for the port 100 shown in FIG. 1 is suitable for subcutaneous implantation. The port 100 includes a body 102, a cap 104 coupled to the body 102, and a septum 106 providing needle access to a chamber 108 defined in the body 102. The chamber 108 includes a delivery opening 110 through a sidewall 109 of the chamber 108 to dispense fluids to desired areas, described in more detail below. The port 100 can be anchored on a desired location within a patient selected by a clinician, such as a bony structure. For example, the body 102 can include one or more openings 112 extending therethrough to receive fasteners to mount the port 100 to the bony structure. As shown, the body 102 and cap 104 can each have a tapered profile with smooth exterior surfaces. This configuration advantageously mitigates skin erosion when the port 100 is implanted in a desired subcutaneous location.

As shown in FIG. 1, the body 102 includes a lower portion 113 having a teardrop-shaped footprint with the chamber 108 formed generally centrally within the circular end of the teardrop-shaped footprint. An exterior surface 114 of the lower portion 113 extends between an upper surface 116 and a bottom wall portion 118 for the body 102. The body 102 further includes an upper portion 119 that includes a wall extending upwardly from the upper surface 116 of the lower portion 113. The body 102 defines an interior cavity 120 having an opening 122 opposite the bottom wall portion 118. In the illustrated form, the body 102 extends around the interior cavity 120 in an annular configuration. The interior cavity 120 includes a lower portion defining the chamber 108 and an upper septum receiving portion 124. The chamber 108 can have smaller cross-sectional dimensions than the upper portion 124, such that a shoulder 126 extends between the upper portion 124 and the chamber 108 of the interior cavity 120. In the illustrated form, the upper portion 124 and the chamber 108 are cylindrical with the chamber 108 having a smaller diameter than the upper portion 124.

Figure 2:
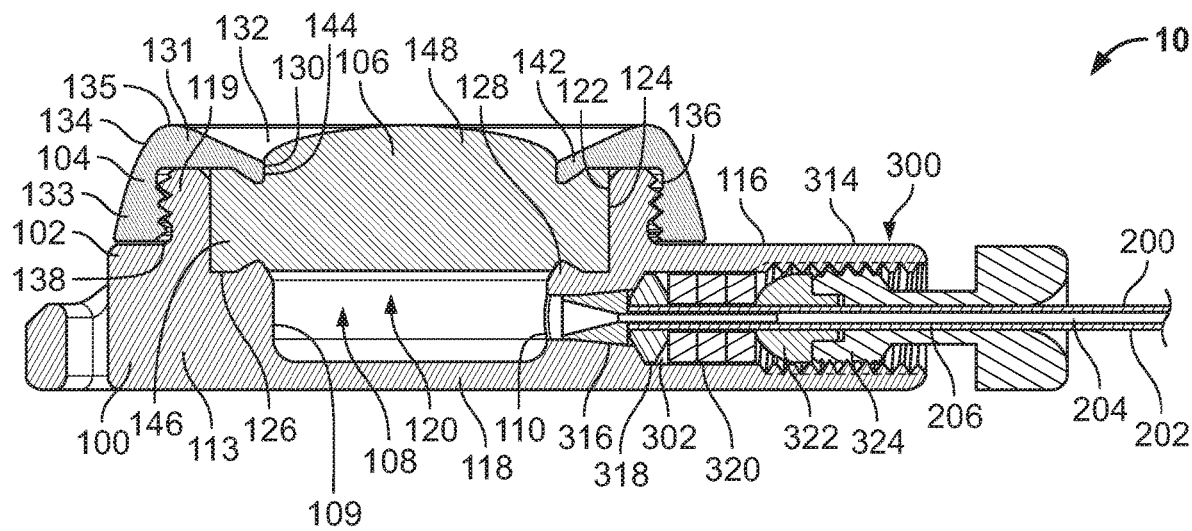
FIG. 2 is a cross-sectional view of the fluid delivery system of FIG. 1 taken along the line 2-2.
Figure 3:
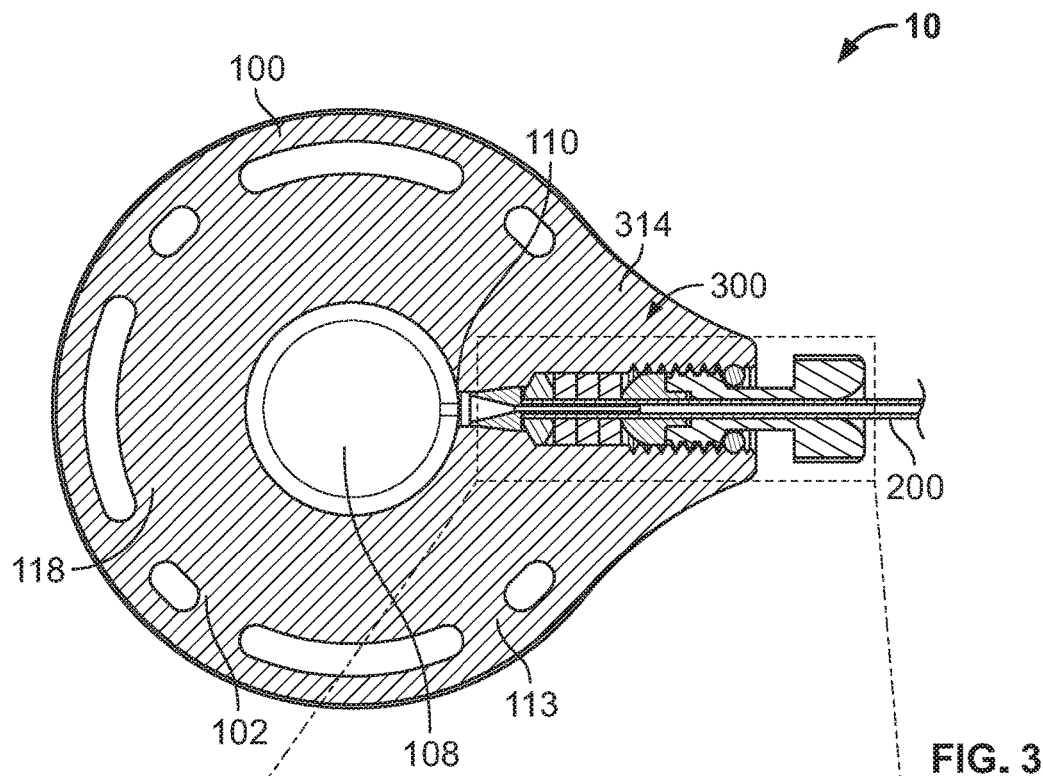
FIG. 3 is a cross-sectional view of the fluid delivery system of FIG. 1 taken along the line 3-3.

The upper portion 124 is sized to receive the septum 106 therein. For example, the septum 106 can have a disk shaped configuration and the diameter of the upper portion 124 can be approximately equal to, e.g., within 2 mm, to the diameter of the septum 106 so that the septum 106 is securely received within the upper portion 124. Further, as shown in FIG. 2, the shoulder 126 can include an upwardly projecting lip 128 that extends around an interior edge thereof and is configured to engage the septum 106.

In order to secure the septum 106 within the port 100, the cap 104 is configured to couple to the upper portion 119 of the body 102 to trap the septum 106 between the cap 104 and the body 102. The cap 104 defines an interior opening 130 extending therethrough to provide needle access to the septum 106. In the illustrated form, the cap 104 has an annular configuration with an upper portion 131 portion having a generally triangular cross-section in a longitudinal direction and a lower skirt portion 133 projecting downward from the upper portion 131. So configured, the cap 104 includes an interior surface 132 that extends around and tapers downwardly toward the opening 130, an exterior surface 134 that tapers downwardly to the body 102, and a top edge 135. As shown, a radially inwardly portion of the cap 104 extends over an upper surface of the septum 106, with the cap 104 deforming the septum 106 and causing the upper surface of the septum 106 to protrude through the opening 130. With this configuration, the interior surface 132 can advantageously redirect a needle that has missed the septum 106 to the opening 130 and to the upper surface of the septum 106.

As shown, an outer surface 136 of the body upper portion 119 can have a threaded configuration and an interior surface 138 of the cap skirt portion 133 can include a corresponding threaded configuration, such that the cap 104 can be threadedly coupled to the body 102 to trap the septum 106 therebetween.

With the cap 104 secured to the body 102, the cap 104 has an annular portion 142 extending over the cavity opening 122 and, in some versions, includes a downwardly projecting lip 144 extending therearound. So configured, an outer portion 146 of the septum 106 is trapped between the annular portion 142 of the cap 104 and the shoulder 126 of the body 102, while a central portion 148 of the septum 106 provides a clear path to the chamber 108. The lips 128, 144 project towards one another on opposite sides of the septum 106 to pinch the septum 106 therebetween to both secure the septum 106 and ensure a fluid tight seal. In some versions, the thickness and diameter of the septum 106 can be optimized to provide a low-profile port 100, while also providing a sufficiently large diameter for the central portion 148 so that the septum 106 can be easily located and identified through tissue.

The catheter 200 can be coupled to the port 100 to be fluidly coupled to the delivery opening 110 of the chamber 108 to dispense fluids to desired areas. The catheter 200 can be utilized to provide homogeneous delivery of composition (optionally comprising one or more therapeutic agents) to the intrathecal space of a patient. As such, the catheter 200 can be configured to extend along the substantially the entire length of a patient's spinal column or along any portion thereof. As shown, the catheter 200 includes an elongate, tubular body 202 having a central passage 204. A proximal end 206 of the catheter 200 is configured to couple to the port 100. As will be understood, the catheter 200 may include any number or configuration of radial and/or distal ports to provide a desired fluid delivery pattern and/or targeted fluid delivery.

The catheter 200 can be configured for long term implantation into a patient and, as such, can be constructed from materials to make the catheter soft, flexible, and kink resistant. Further, in some versions, the catheter 200 can be configured to complex spine patients, e.g., scoliosis, the materials can provide column strength, break resistance, and stiffness so that the catheter 200 can be threadable during insertion. Pursuant to this, the catheter 200 can include a reinforcement layer or reinforced sidewall at least in the proximal end 206 to increase a hoop strength of the catheter 200, i.e., a strength of the catheter resisting crushing damage from a compressive force. This can advantageously be utilized to provide a strong connection and seal with the port 100. In some examples, the catheter size can range from 0.5 mm to 5 mm.

Details of the connection assembly 300 configured to fluidly couple the port 100 and the catheter 200 are shown in FIGS. 2-11. The components of the assembly 300 and the dimensions thereof can be configured to allow assembly without significant pre-compression of the assembly 300. Further, the configuration described can target an optimal compression during assembly and catheter connection. For example, the assembly 300 described herein can produce an axial compression in a range of about 0.08 inches and about 0.09 inches, and more particularly about 0.84 inches.

The port 100 defines a cylindrical cavity 302 sized to receive components of the assembly 300 therein. The cavity 302 extends radially through the body 102 with the delivery opening 110 at an interior end 304 and an open exterior end 306. As shown, the cavity 302 can include portions sized and shaped to receive the various components of the assembly 300 therein, as described below. In the illustrated example, the cavity 302 includes an innermost portion 308 having the delivery opening 110 at one end thereof, an intermediate portion 310, and an outer portion 312. As previously discussed, the port body 102 can have a teardrop-shaped configuration with a projecting portion 314 extending radially outward from the generally circular central portion defining the chamber 108. So configured, the cavity 302 can be disposed within the projecting portion 314.

The assembly 300 further includes a stem member 316, a washer 318, a gasket 320, which in the illustrated form is a plurality of o-rings, an engagement tip 322, and a connector 324, which interact to fluidly couple the catheter 200 to the port 100. The stem member 316 includes a base portion 326 and an elongate stem portion 328 extending outwardly from the base 326. A passage 330 extends longitudinally through the base and stem 326, 328 so that fluid can flow longitudinally through the stem member 316. The passage 330 can include a mouth 332 that extends around the delivery opening 110 and narrows to the portion within the stem 328. In the illustrated form, the mouth 332 has a conical shape narrowing to the passage 330 within the stem 328.

As shown, the innermost portion 308 of the cavity 302 is sized to receive the base 326 of the stem member 316 therein with the stem 328 extending radially within the cavity 302 away from the chamber 108. In order to restrict movement of the stem member 316 relative to the port 100, the base 326 and cavity innermost portion 308 can have complementary surfaces so that the base 326 can seat within the cavity portion 308. For example, the base 326 can have a frusto-conical configuration with an inwardly tapering exterior surface 334 and the cavity innermost portion 308 can have a complementary inwardly tapering surface 336, such that the base portion 326 can be radially inserted into the cavity innermost portion 308 toward the chamber 108 until further radial movement is restricted by the surfaces 334, 336 engaging one another. With this configuration, the catheter 200 can be inserted into the cavity 302 and over the stem 328 so that the stem 328 extends within the central passage 204 of the catheter 202 and the proximal end 206 abuts the base 326. The dimensions of the stem 328 can have a small clearance with respect to an inner diameter of the catheter 200 to provide an easy assembly, while also providing a secure connection therewith when the catheter 200 is compressed onto the stem 328. In one form, an exterior surface of the stem 328 can have a textured configuration that grips the inner surface of the catheter 202 when the stem 328 is inserted therein and the o-rings 320 are compressed therearound. For example, the stem 328 can have a sand/grit blasted or equivalent exterior surface, a distribution of small cuts or protrusions, and so forth. In an additional or alternative form, inner surfaces of the o-rings 320 can have a textured configuration.

Each of the washer 318, one or more o-rings 320, engagement tip 322, and connector 324 include a central opening 338 extending therethrough so that the catheter 200 can extend through each of the components within the cavity 302. For ease of installation, the diameters of the central openings 338 can be larger than an outer diameter of the catheter 200. Further, as shown, when the catheter 200 is inserted into the central openings 338 and through the components of the assembly 300, the catheter 200 is aligned with the delivery opening 110 and positioned generally centrally within the cavity 302.

As shown, the innermost portion 308 of the cavity 302 can have a smaller diameter than the intermediate portion 310 so that a shoulder surface 340 is defined within the cavity 302 extending therebetween. So configured, when the washer 318 is inserted into the cavity 302, the washer 318 abuts the shoulder surface 340 restricting further movement of the components of the assembly 300. Further, the outer portion 312 of the cavity 302 can have a threaded configuration and the connector 324 can include a corresponding threaded portion 342 so that the connector 324 can be threaded into the cavity 302. With this configuration, to secure the catheter 200 to the port 100 and create a fluid tight seal, the connector 324 can engage the thread of the cavity outer portion 312 and be rotated to compress the o-rings 320 between the washer 318 and the engagement tip 322. This causes the o-rings 320 to compress and radially expand to tightly engage the surface of the cavity 302 and the catheter 200, which compresses the catheter 200 around the stem 328. As such, the catheter 200 is held within the cavity 302 by components tightly engaging both the interior of the central passage 204 and the exterior of the body 202. In the illustrated form, the assembly 300 includes three o-rings 320, but other numbers can be utilized, such as one, two, four, five, or more. It has been found that utilizing multiple o-rings 320 provide multiple points of contact with the catheter 200 that deform homogeneously to achieve a target and uniform compression.

Figure 4:
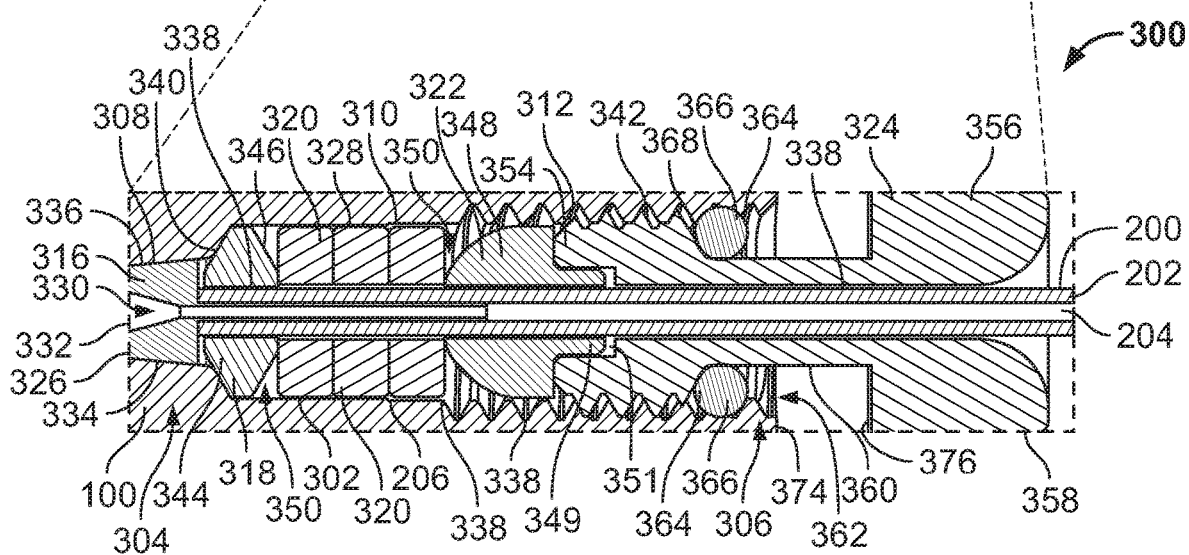
FIG. 4 is a sectional view of the port, catheter, and connection assembly of FIG. 3.
Figure 5:
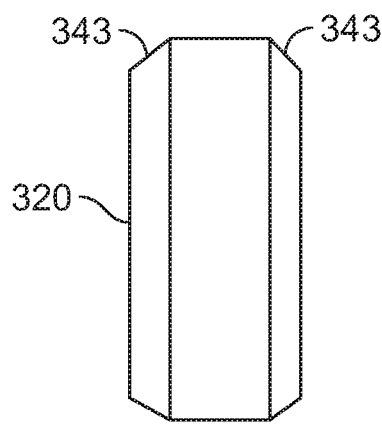
FIG. 5 is a top plan view of a first alternative o-ring for the connection assembly of FIG. 3.
Figure 6:
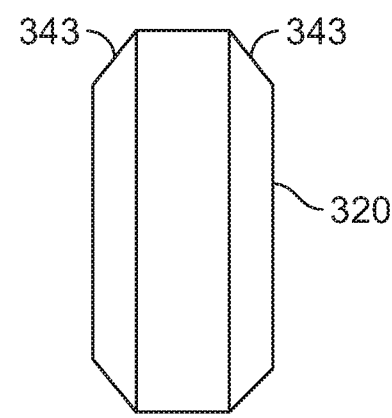
FIG. 6 is a top plan view of a second alternative o-ring for the connection assembly of FIG. 3.

Alternative configurations for the o-rings 320 are shown in FIGS. 5 and 6. Rather than an o-ring 320 configured as shown in FIG. 4 with planar sides, the assembly 300 can alternatively be provided with o-rings 320 that have chamfered edges 343. In two example configurations, the chamfered edges 343 can extend along a 15 degree angle as shown in FIG. 5 or a 25 degree angle as shown in FIG. 6. Other angles are also suitable. Although both edges 343 of the embodiments shown in FIGS. 5 and 6 are chamfered, it will be understood that one of the sides can be planar, if desired. Further, the edges can alternatively have a rounded configuration.

If desired, as shown in FIG. 4, the shoulder surface 340 and a seat surface 344 of the washer 318 facing the chamber 108 can have complementary surface configurations, such as an inwardly tapered chamfered surface as shown, curved, etc., so that the washer 318 can seat within the shoulder surface 340 in an end of the intermediate portion 310.

In some versions, one or both compression surfaces 346, 348 of the washer 318 and engagement tip 322 facing the o-rings 320 can have a contoured configuration providing one or more axial deformation or relief spaces 350 for the o-rings 320 when the assembly 300 is tightened. This allows the o-rings 320 to be deformed to engage the cavity 302 and catheter 200, but also to deform axially in predetermined and desired configurations into the relief spaces 350. For example, one or both compression surfaces 346, 348 can have a tapered configuration and/or a curved configuration. In the illustrated form, the washer compression surface 346 engages the adjacent o-ring 320 around the central opening 338 therethrough and has a chamfered configuration that tapers away from the o-rings 320 and the engagement tip compression surface 348 engages the adjacent o-ring 320 around the central opening 338 therethrough and has a curved configuration. The curved configuration can be convex, such as a bullet shape as shown, or concave as desired. Of course, it will be understood that the configurations of compression surfaces 346, 348 can be switched or can be the same.

Figure 7:
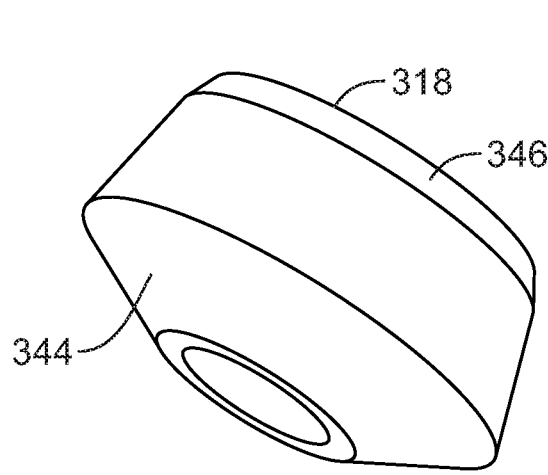
FIG. 7 is a perspective view of a first alternative washer for the connection assembly of FIG. 3.
Figure 8:
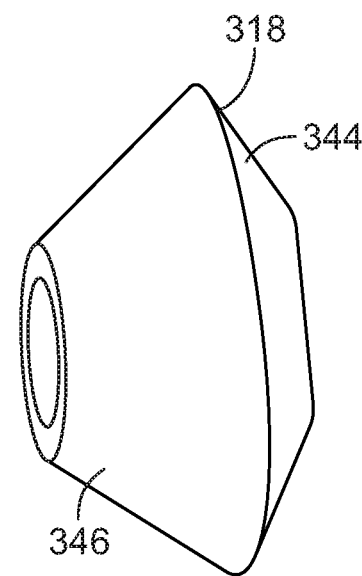
FIG. 8 is a perspective view of a second alternative washer for the connection assembly of FIG. 3.
Figure 9:
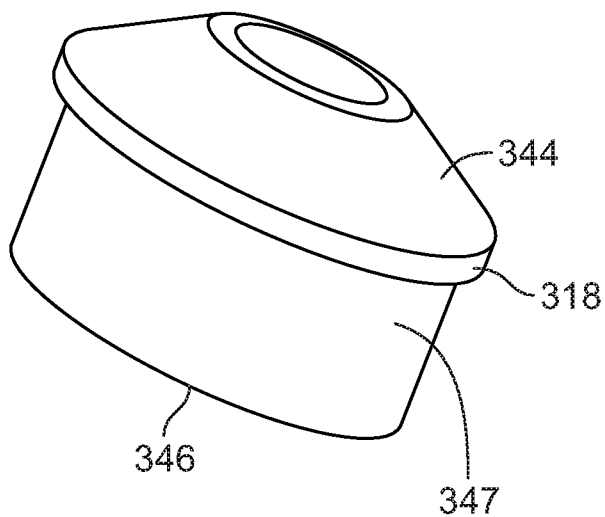
FIG. 9 is a perspective view of a third alternative washer for the connection assembly of FIG. 3.

Alternative configurations for the washer 318 are shown in FIGS. 7-9. Rather than the washer 318 having generally symmetrical frusto-conical surfaces 344, 346 configured as shown in FIG. 4, as shown in FIGS. 7 and 8, the washer 318 can alternatively have offset frusto-conical surfaces 344, 346 where one of the surfaces 344, 346 extends along a more acute angle with respect to the other of the surfaces 344, 346. In another example shown FIG. 9, the washer 318 can have a stepped configuration with a reduced diameter portion 347 so that the compression surface 346 has a smaller diameter relative to the cavity 302, which provides an annular relief space 350. Further, the frusto-conical surfaces can alternatively have a rounded configuration.

Figure 10:
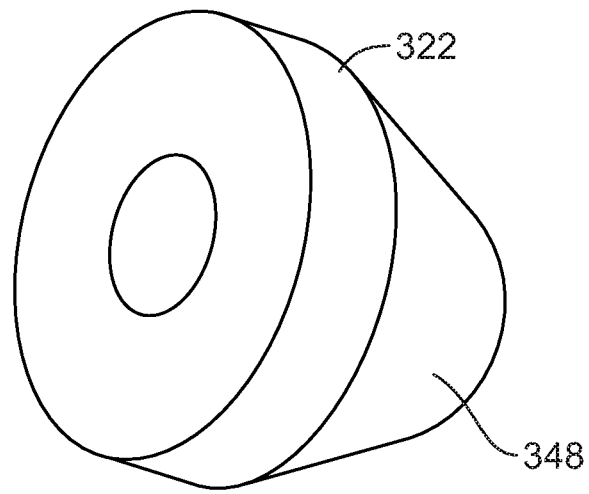
FIG. 10 is a perspective view of a first alternative engagement tip for the connection assembly of FIG. 3.
Figure 11:
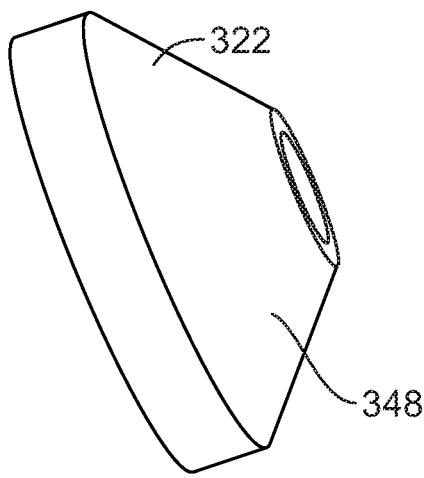
FIG. 11 is a perspective view of a second alternative engagement tip for the connection assembly of FIG. 3.

Alternative configurations for the engagement tip 322 are shown in FIGS. 10 and 11. Rather than the engagement tip 322 having a curved compression surface 348 configured as shown in FIG. 4, the engagement tip 322 can alternatively have a frusto-conical compression surface 348.

In the illustrated form, the connector 324 and engagement tip 322 are separate components. This allows the rotation of the connector 324 as it is threaded into the cavity 302 to not be imparted to the engagement tip 322 or to be minimally imparted to the engagement tip 322 due to friction, for example. As such, rotational engagement between the engagement tip 322 and the adjacent o-ring 320, and the resulting friction and/or binding, is minimized, which controls the deformation of the o-ring 320 to desirable shapes and areas. If desired, the engagement tip 322 and connector 324 can have cooperating structure to maintain the alignment of the engagement tip 322 within the cavity 302. For example, the engagement tip 322 and connector 324 can have a stepped configuration therebetween. As shown, the engagement tip 322 can include a rearwardly extending collar 349 and the connector 324 can include an axial counterbore 351 in the threaded portion 342 thereof sized to receive the collar 349. Of course, it will be understood that in some versions the connector 324 and engagement tip 322 can be integral portions of a single piece component.

Figure 12:
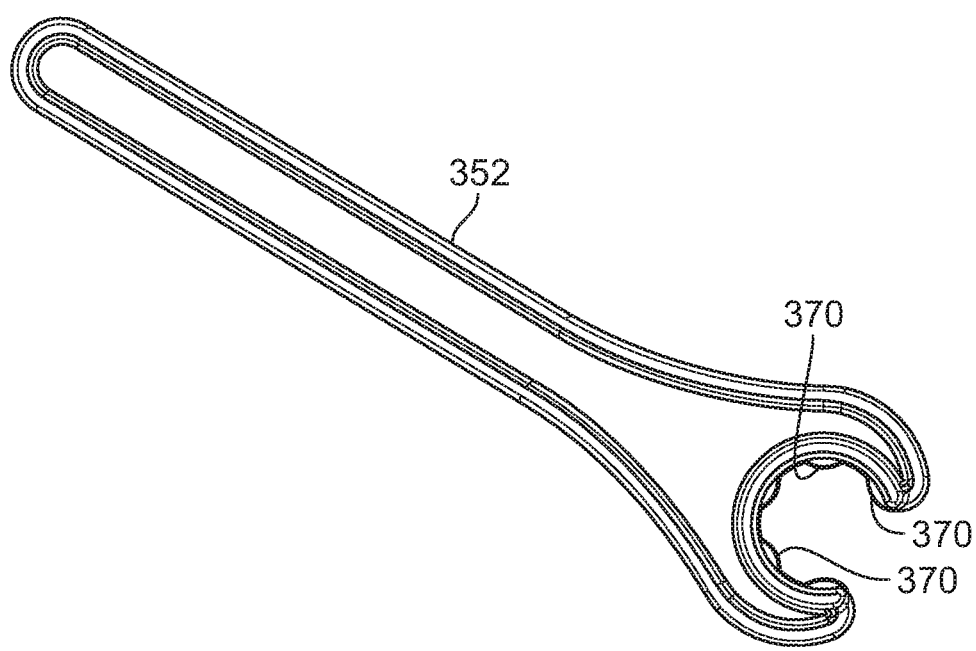
FIG. 12 is a perspective view of a tool for the connection assembly of FIG. 1.
Figure 13:
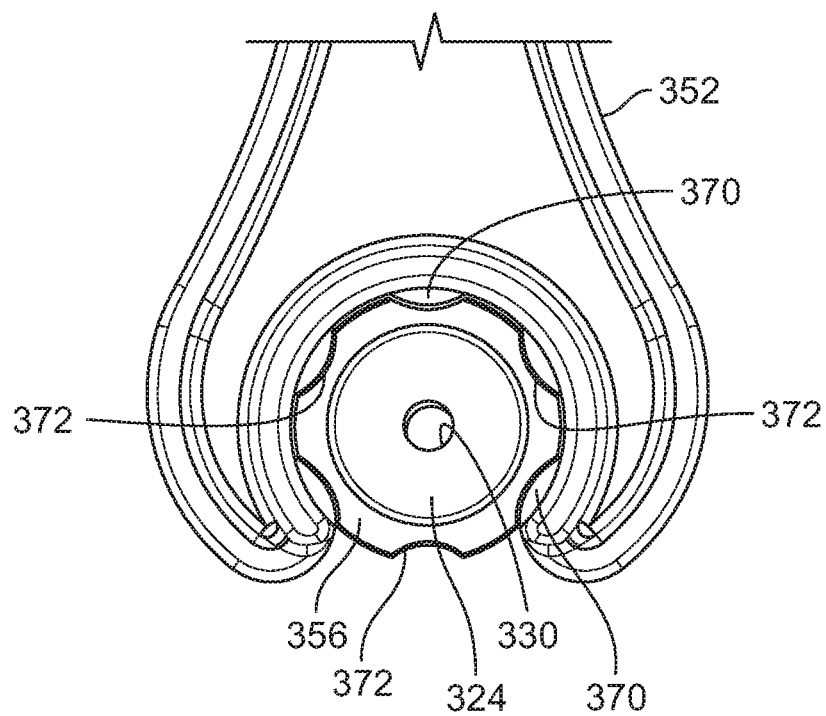
FIG. 13 is a sectional view of the tool of FIG. 5 engaging a connector of the connection assembly of FIG. 1.

Additional details for the connector 324 and an optional tool 352 are shown in FIGS. 4, 12, and 13. In the illustrated form, in addition to the threaded portion 342 at a proximal end 354, the connector 324 can include a tool interface 356 at a distal end 358 and a neck portion 360 extending between the threaded portion 342 and the tool interface 356. If desired, the central opening 338 through the tool interface 356 can have a fluted exit configuration 361, which provided a curved surface as the catheter 200 exits the assembly 300. The curved surface reduces the stress and strain that might be applied to the catheter 200, as compared to an edge, when the catheter 200 is moved relative to the port 100.

The neck portion 360 reduces the radius of the connector 324 relative to the threaded portion 342, which creates an annular radial space 362 within the cavity 302 when the connector 324 is threaded into the cavity 302. Advantageously, this radial space 362 can be utilized to hold the assembly 300 in position in an assembled configuration with all the components received within the cavity 302. Pursuant to this, one or more bores 364 can extend through the body 102 into the cavity 302 in a direction transverse to the longitudinal axis of the cavity 302, such as generally perpendicular as shown. Next, one or more retention members 366 can be inserted into the bores 364 after the connector 324 is partially threaded into the cavity 302 so that the retention members 366 extend into the radial space 362 adjacent to the neck portion 360. In the illustrated form, the port 100 includes two bores 364 aligned so that two retention members 366 can be inserted into the cavity 302 on opposing sides of the connector neck portion 360.

The retention members 366 can be configured to be permanently mounted within the bores 364, such as by friction fit, deformation, e.g., mushrooming, ultrasonic welding, and so forth, so that the connector 324, and therefore the remaining components of the assembly 300, are permanently retained within the cavity 302. In other words, if the connector 324 inadvertently unthreads from the cavity 302, the retention members 366 will abut a stop surface 368 of the threaded portion 342 that transitions to the neck portion 360. This prevents the components from falling out of the cavity 302 when the port 100 is being handled or having to deal with manipulating and inserting the small components of the assembly 300 in situ or other awkward situations. Rather, a user can assemble the components of the assembly 300, insert the components into the cavity 302, and subsequently insert the one or more retention members 366 into the bores 364 to ensure that the assembly 300 is ready for subsequent installation. In the configuration shown in FIG. 4, the assembly 300 is in an uncompressed state, it will be understood that the bore 364 and retention member 366 configuration can coincide with partially compressed states, or a fully compressed state if desired.

Details of the tool 352 and tool interface 356 are shown in FIGS. 12 and 13. As discussed above, the system 10 can optionally be provided with the tool 352 to aid a user in tightening the connector 324 within the cavity 302 to thereby compress the o-rings 320 and retain the catheter 200 within the assembly 300. Pursuant to this, the tool 352 and tool interface 356 can have complementary structures 370, 372 that engage one another and allow the tool 352 to turn the connector 324. For example, the tool interface 356 can be generally cylindrical and the tool 352 can be a wrench having a mouth configured to extend around a circumference of the tool interface 352. Further, the wrench 352 can be provided with the structures 370 on an interior surface thereof and the structures 372 of the tool interface 356 can be provided on an exterior surface thereof. Further, in some versions, the structures 370, 372 can be configured to provide a torque-limiting functionality. Specifically, the structures 370, 372 can be sized and shaped to slip or otherwise fail when a force is applied to the tool that exceeds a predetermined force threshold. The predetermined force threshold can correspond to a maximum compression force to be applied to the o-rings 320. Advantageously, with this configuration, it can be ensured that user does not over tighten the connector 324 within the cavity 302 to thereby overcompress the o-rings 320, as any force that would exceed a desired compression will cause the engagement between the connector 324 and the tool 352 to slip.

In the illustrated form, the structures 370 of the tool 352 can have a scalloped configuration with spaced rounded protrusions and the structures 372 of the tool interface 356 can be recesses sized and spaced to receive the scalloped protrusions of the tool 352 therein. Of course, it will be understood that the scalloped configuration and recesses can be provided on the opposite structure. Further, other engagement structures can also be utilized.

In a further, or alternative, configuration to limit overcompression, the axial thickness of the washer 318, o-rings 320, and engagement tip 322, the axial depth of the cavity 302, and the length of the connector 324 through the threaded and neck portions 342, 360 can be configured to limit a depth that the connector 324 can be screwed into the cavity 302. For example, the tool interface 356 can have a diameter greater than an inner diameter of the cavity 302, so that a stop surface 376 of the connector 324 defined by the tool interface 356 can engage an exterior surface 374 of the port body 102 around the cavity opening 306. Advantageously, the assembly 300 can be configured so that when the connector 324 is screwed into the cavity 302 until the stop surface 376 abuts the exterior surface 374, an optimal compression is applied to the assembly 300.

In some examples, the o-rings 320 can be made from suitable plastic/polymeric materials; the stem member 316 can be made from Titanium, Stainless Steel, other suitable metals, or a suitable plastic; the port body 102 can be made from Titanium, Stainless Steel, Polyether ether ketone (PEEK), or other suitable plastic; the connector 324, washer 318, and engagement tip 322 can be made from PEEK, Titanium, Stainless Steel, other suitable metal or plastic, or combinations thereof.

It will be appreciated that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. The same reference numbers may be used to describe like or similar parts. Further, while several examples have been disclosed herein, any features from any examples may be combined with or replaced by other features from other examples. Moreover, while several examples have been disclosed herein, changes may be made to the disclosed examples within departing from the scope of the claims.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

We claim:

1. A fluid delivery system comprising:
    a body defining a cavity therein, the cavity having a cylindrical configuration with a delivery opening at a proximal end and an open distal end, the cavity defining a seat surface that extends radially inwardly into the cavity adjacent to the delivery opening and a threaded portion adjacent to the open distal end;
    a catheter connection assembly disposed within the cavity and configured to couple a catheter to the body, the catheter connection assembly comprising:
        a washer configured to abut the seat surface;
        a gasket;
        an engagement tip disposed on an opposite side of the gasket from the washer; and
        a connector having an external thread configured to engage the threaded portion of the cavity and a tool engagement end with an exterior radial surface; and
    a wrench having a mouth configured to extend around the tool engagement end of the connector, an interior surface of the mouth and the exterior radial surface of the tool engagement end comprising complementary structures such that the wrench is configured to tighten the connector into the cavity, wherein the complementary structures are configured to slip out of engagement with one another upon the application of a rotational force to the wrench greater than a threshold force; and wherein the washer, gasket, engagement tip, and connector each define a central passage extending therethrough for reception of the catheter; and the catheter connection assembly is configured such that when the connector is threaded into the cavity, the connector causes the engagement tip and washer to compress the gasket therebetween to thereby radially compress the gasket around the catheter to retain the catheter within the cavity.

2. The fluid delivery system of claim 1, wherein the cavity comprises an inner portion extending from the seat surface to the delivery opening; and the catheter connection assembly further comprises a stem member having a base portion and a stem portion extending outwardly from the base portion, the stem member configured to be disposed within the inner portion of the cavity such that the stem portion extends longitudinally within the cavity away from the delivery opening into the catheter that is inserted through the washer, gasket, engagement tip, and connector.

3. The fluid delivery system of claim 2, wherein the stem portion has a length to extend through the washer and gasket and into the central passage of the engagement tip, such that the stem portion braces the catheter along a portion thereof compressed by the gasket when then connector is threaded into the cavity.

4. The fluid delivery system of claim 2, wherein the inner portion of the cavity and the base portion of the stem member have complementary contoured surfaces, such that the base seats within the inner portion of the cavity and is restricted from longitudinal movement within the cavity toward the delivery opening.

5. The fluid delivery system of claim 1, wherein the gasket comprises a plurality of o-rings.

6. The fluid delivery system of claim 1, wherein the seat surface of the cavity extends rearwardly along a longitudinal axis thereof; and an inner surface of the washer has a complementary chamfered configuration such that the washer nests within the seat surface.

7. A fluid delivery system comprising:
a body defining a cavity therein, the cavity having a cylindrical configuration extending along a longitudinal axis with a delivery opening at a proximal end and an open distal end, the cavity defining a seat surface that extends radially inwardly into the cavity adjacent to the delivery opening and a threaded portion adjacent to the open distal end;
a catheter connection assembly disposed within the cavity and configured to couple a catheter to the body, the catheter connection assembly comprising:
a washer configured to abut the seat surface;
a gasket;
an engagement tip disposed on an opposite side of the gasket from the washer; and
a connector having an external thread configured to engage the threaded portion of the cavity;
wherein the washer, gasket, engagement tip, and connector each define a central passage extending therethrough for reception of a catheter; and the catheter connection assembly is configured such that when the connector is threaded into the cavity, the connector causes the engagement tip and washer to compress the gasket therebetween to thereby radially compress the gasket around the catheter to retain the catheter within the cavity; and wherein compression surfaces of the engagement tip and the washer engage the gasket on opposite sides thereof; and at least one of the compression surfaces of the engagement tip and the washer has a contoured configuration extending away from the gasket along the longitudinal axis to thereby provide deformation space for the gasket as the gasket is compressed.

8. The fluid delivery system of claim 7, wherein the compression surfaces of both the engagement tip and the washer have contoured configurations extending away from the gasket to thereby provide deformation spaces for the gasket on both sides thereof.

9. The fluid delivery system of claim 7, wherein the compression surface of at least one of the engagement tip or the washer has a bulleted configuration.

10. The fluid delivery system of claim 7, wherein the compression surface of at least one of the engagement tip or the washer has a chamfered configuration.

11. The fluid delivery system of claim 1, wherein the engagement tip and the connector comprise a single-piece component.

12. The fluid delivery system of claim 1, wherein the engagement tip and connector are separate components.

13. The fluid delivery system of claim 12, wherein the engagement tip and connector have a stepped connection therebetween, one of the engagement tip or the connector comprising a counterbore and the other of the engagement tip or the connector comprising a collar configured to be received within the counterbore.

14. The fluid delivery system of claim 1, wherein the connector further comprises a throat portion having a reduced diameter as compared to the threaded portion; and the body further comprises a bore opening radially into the cavity; and further comprising a retention member configured to be inserted into the bore to extend along the throat portion rearwardly of the threaded portion to thereby retain the connector within the cavity.

15. A fluid delivery system of claim 1, comprising:
a body defining a cavity therein, the cavity having a cylindrical configuration with a delivery opening at a proximal end and an open distal end, the cavity defining a seat surface that extends radially inwardly into the cavity adjacent to the delivery opening and a threaded portion adjacent to the open distal end;
a catheter connection assembly disposed within the cavity and configured to couple a catheter to the body, the catheter connection assembly comprising:
a washer configured to abut the seat surface;
a gasket;
an engagement tip disposed on an opposite side of the gasket from the washer; and
a connector having an external thread configured to engage the threaded portion of the cavity;
wherein the washer, gasket, engagement tip, and connector each define a central passage extending therethrough for reception of a catheter; and the catheter connection assembly is configured such that when the connector is threaded into the cavity, the connector causes the engagement tip and washer to compress the gasket therebetween to thereby radially compress the gasket around the catheter to retain the catheter within the cavity;
wherein the connector further comprises a tool engagement end having a diameter larger than the cavity such that the tool engagement end defines a stop surface configured to engage the body when the connector is fully threaded into the cavity.

16. The fluid delivery system of claim 15, wherein the central passage extending through the tool engagement end of the connector comprises a fluted configuration.

17. The fluid delivery system of claim 15, further comprising a wrench having a mouth configured to extend around the tool engagement end, wherein an exterior radial surface of the tool engagement end of the connector and an interior surface of the mouth comprise complementary structures such that the wrench is configured to tighten the connector into the cavity.

18. The fluid delivery system of claim 17, wherein the complementary structures are configured to slip out of engagement with one another upon the application of a rotational force to the wrench greater than a threshold force.

19. The fluid delivery system of claim 1, wherein the body comprises a port implantable to a subcutaneous location, the port defining a chamber having an open top and the delivery opening and a septum extending over the open top of the chamber.

20. The fluid delivery system of claim 19, further comprising a catheter extending through the washer, gasket, engagement tip, and connector, the gasket being compressed around a proximal end of the catheter to retain the catheter within the cavity and fluidly couple the catheter to the chamber of the port.

21. The fluid delivery system of claim 1, wherein the complementary structures comprise ribs and indentations.

\* \* \* \* \*